United States Patent
Kohnke et al.

(10) Patent No.: US 10,799,480 B2
(45) Date of Patent: Oct. 13, 2020

(54) CALIXPYRROLE-BASED ANTITUMOR COMPOUNDS

(71) Applicant: Giam Pharma International sarl, Monthey (CH)

(72) Inventors: Franz Heinrich Kohnke, Messina (IT); Alberto Izzotti, Messina (IT); Camillo Rosano, Messina (IT); Grazia Cafeo, Messina (IT)

(73) Assignee: Giam Pharma International SARL., Monthey (CH)

( * ) Notice: Subject to any disclaimer, the term of this patent is extended or adjusted under 35 U.S.C. 154(b) by 0 days.

(21) Appl. No.: 16/337,532

(22) PCT Filed: Sep. 26, 2017

(86) PCT No.: PCT/IT2017/000205
§ 371 (c)(1),
(2) Date: Mar. 28, 2019

(87) PCT Pub. No.: WO2018/061045
PCT Pub. Date: Apr. 5, 2018

(65) Prior Publication Data
US 2019/0224167 A1    Jul. 25, 2019

(30) Foreign Application Priority Data
Sep. 29, 2016 (IT) .................... 102016000097521

(51) Int. Cl.
| | |
|---|---|
| C07D 487/22 | (2006.01) |
| A61K 31/409 | (2006.01) |
| A61K 47/64 | (2017.01) |
| A61K 47/68 | (2017.01) |
| A61P 35/00 | (2006.01) |
| A61K 47/69 | (2017.01) |

(52) U.S. Cl.
CPC ............ A61K 31/409 (2013.01); A61K 47/64 (2017.08); A61K 47/6801 (2017.08); A61P 35/00 (2018.01); C07D 487/22 (2013.01); A61K 47/6923 (2017.08); A61K 47/6931 (2017.08)

(58) Field of Classification Search
CPC .................................................. C07D 487/22
See application file for complete search history.

(56) References Cited

PUBLICATIONS

Cafeo, G. et al., "Drug Delivery with a Calixpyrrole-trans-Pt (II) Complex", Journal of the American Chemical Society, vol. 135, No. 7, Feb. 20, 2013, 2544-2551.
Cafeo, G. et al., "Host-Guest Chemistry of Aromatic-Amide-Linked Bis- and Tris-Calix[4]pyrroles with Bis-Carboxylates and Citrate Anion", Chemistry—A European Journal, vol. 20, No. 6, Jan. 8, 2014, 1658-1668.
Lappano, R. et al., "A calixpyrrole derivative acts as an antagonist to GPER, a G-protein coupled receptor: mechanisms and models", Disease Models & Mechanisms, vol. 8, No. 10, Jul. 16, 2015, 1237-1246.
Sloan, K.B., Wasdo S.C. (2007) Topical Delivery Using Prodrugs. In: Stella V.J., Borchardt R.T., Hageman M.J., Oliyai R., Maag H., Tilley J.W. (eds) Prodrugs. Biotechnology: Pharmaceutical Aspects, vol. V. Springer, New York, NY.
International Search Report, dated Feb. 8, 2018, PCT/IT2017/000205.

*Primary Examiner* — Brian E McDowell
(74) *Attorney, Agent, or Firm* — Elmore Patent Law Group, P.C.; Carolyn Elmore; Joseph Zucchero

(57) ABSTRACT

Calixpyrrole-based antitumor compounds such as compounds of Formula IX:

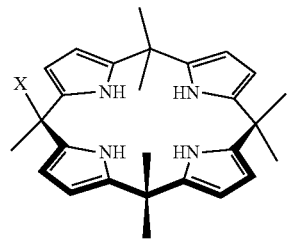

are described, which can be derivatized to obtain their passive transport on tumor masses through the Enhanced Permeation and Retention, EPR, effect of the neoplastic vasculature. The conjugation of the above-mentioned compounds with peptides/antibodies is further described, for their possible active transport on tumor cells.

3 Claims, 9 Drawing Sheets

CALIXPYRROLE-BASED ANTITUMOR COMPOUNDS

The present invention refers to calixpyrrole-based antitumor compounds, which can be derivatized to obtain their passive transport on tumor masses through the Enhanced Permeation and Retention, EPR, effect of the neoplastic vasculature.

The present invention further refers to the conjugation of the above described compounds with peptides/antibodies for their possible active transport on tumor cells.

Calixpyrroles are a subset of a class of macrocycles which were previously called porphyrinogens. Porphyrinogens are non-conjugated macrocyclic species composed of four pyrrole rings connected in position alpha through $sp^3$ hybridized carbon atoms.

Several patents and publications deal with calixpyrroles (for example, WO-A-97/37995): however, none of these documents contains a documental proof of an antitumor activity of any derivative. WO-A-97/37995 mentioned the chances that calixpyrrole derivatives can have uses in the administration of drugs and in oncology, but this is expressed merely as a "concept", while no concrete example is provided which avails such assumption. In oncology, there are macrocyclic compounds containing pyrrole, which, however, are very different from calixpyrroles (for example, porphyrins and texaphyrins).

The inventors of the present Application have performed, during the past 15 years, numerous biologic assays on the pro-apoptotic activities of a variety of calixpyrroles. The discovered activities have generally been demonstrated as 'non cytotoxic': for example, the simplest compound in this class, meso-octametil-calix[4]pyrrole, has not appeared as cytotoxic, but instead has resulted a selective inhibitor of the extrogen receptor GPER (R. Lappano, A. Pisano, M. F. Santolla, F. E. M. De, M. P. De, V. Dolce, M. Maggiolini, C. Rosano, M. Ponassi, L. Felli, G. Cafeo, F. H. Kohnke, S. Abonante, *Dis Model Mech* 2015, 8, 1237). Other studies performed on the use of calixpyrroles, such as systems for administering drugs for the trans-platinum, have demonstrated that numerous other calixpyrrole derivatives are not cytotoxic (G. Cafeo, G. Carbotti, A. Cuzzola, M. Fabbri, S. Ferrini, F. H. Kohnke, G. Papanicolau, M. R. Plutino, C. Rosano, A. J. P. White, *J. Am. Chem. Soc.* 2013, 135, 2544). These studies demonstrate that the activity of the compounds discovered by the inventors of the present Application is confined to specific structures, as described below.

Object of the present invention is solving the above prior art problems, by providing calixpyrrole-based antitumor compounds, which can be used as such or be derivatized to obtain their passive transport on tumor masses through the Enhanced Permeation and Retention, EPR, effect of the neoplastic vasculature.

A further object of the present invention is providing antitumor compounds as described above, which can be conjugated with peptides/antibodies for their possible active transport on tumor cells.

The above and other objects and advantages of the invention, as will appear from the following description, are obtained with calixpyrrole-based antitumor compounds as claimed in claim 1. Preferred embodiments and non-trivial variations of the present invention are the subject matter of the dependent claims.

It is intended that all enclosed claims are an integral part of the present description.

It will be immediately obvious that numerous variations and modifications (for example related to shape, sizes, arrangements and parts with equivalent functionality) can be made to what is described, without departing from the scope of the invention as appears in the enclosed claims.

The present invention will be better described by some preferred embodiments thereof, provided as a non-limiting example, with reference to the enclosed drawings, in which.

Figure 11:
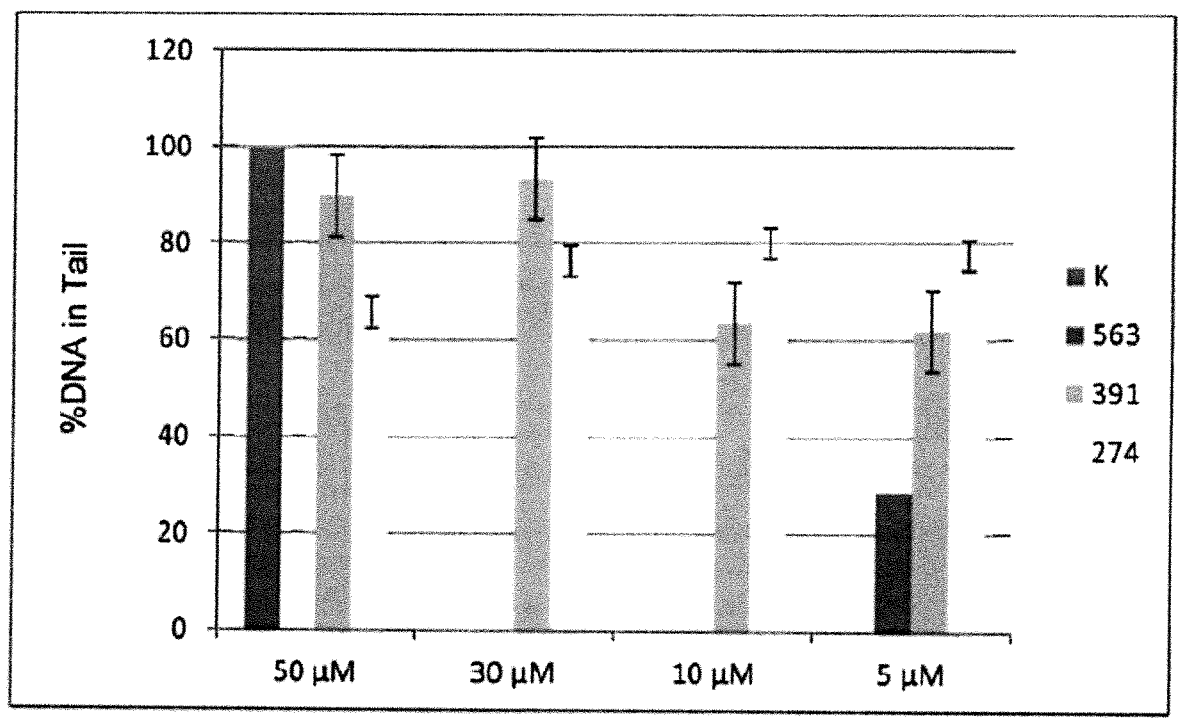
Figure 12:
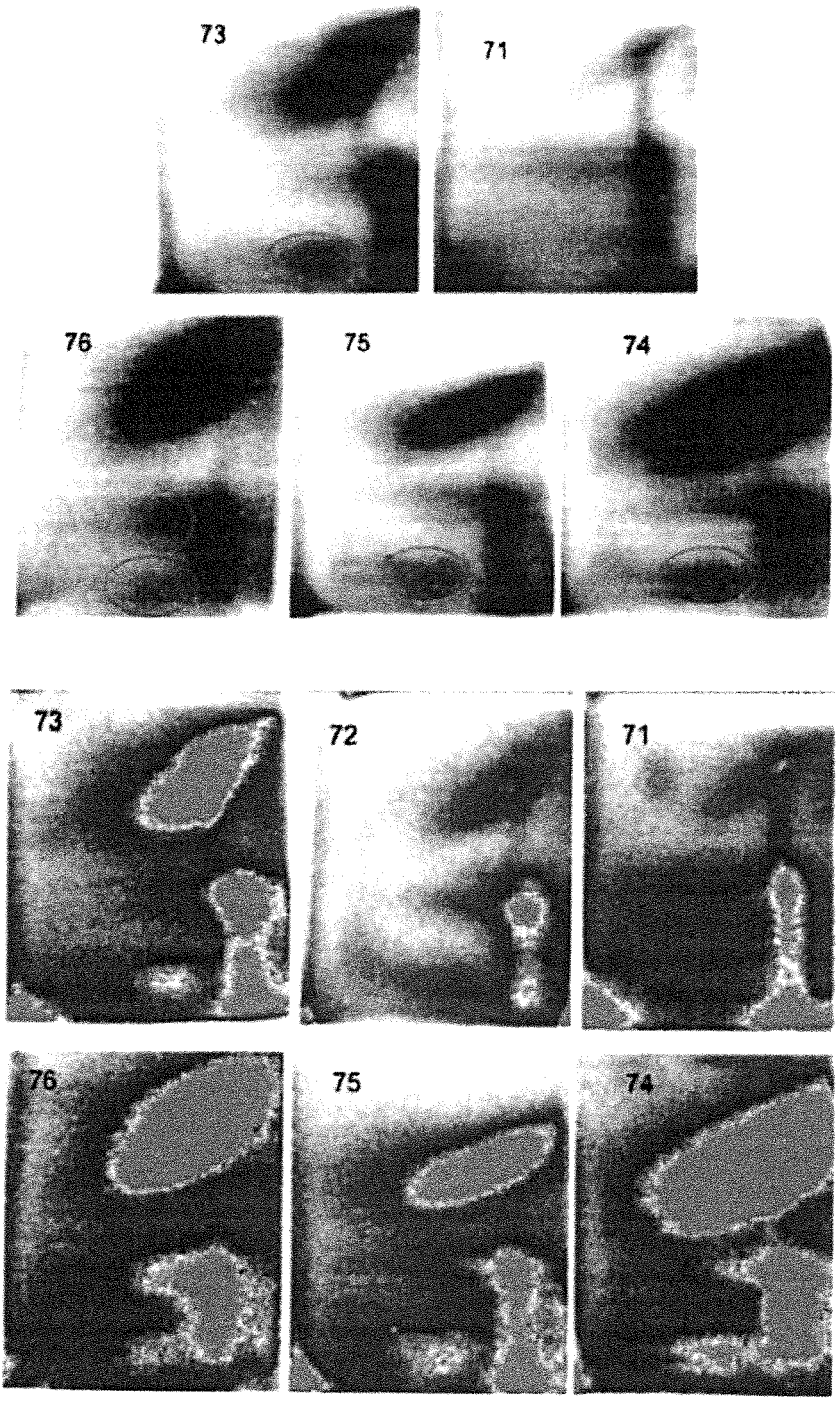

FIG. 11 shows the results of COMET tests performed on cellular lines of pulmonary carcinoma A549, with K as control; and FIG. 12 shows the receptor-DNA adducts obtained through 32P marking for treating cellular lines of pulmonary carcinoma A549 with the compounds of Formulas III (panels 73 and 74) and I (panels 75 and 76); panel 71 shows the control; the red circles point out the adducts present only in cells treated with the compounds.

The invention first of all deals with a calixpyrrole-based antitumor compound from Formula I:

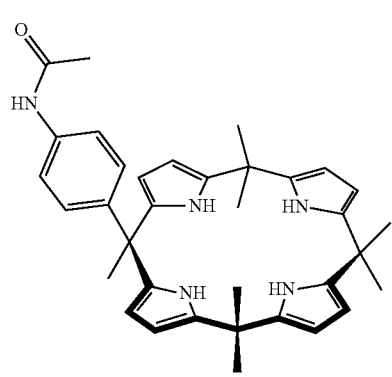

I such antitumor compound being adapted to be used as such or derivatized to obtain its passive transport on tumor masses through an Enhanced Permeation and Retention, EPR, effect of the neoplastic vasculature.

The antitumor compound according to Formula I has also a derivative from Formula II:

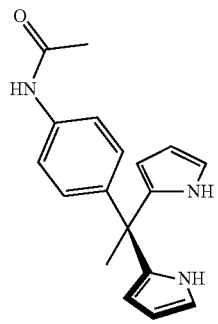

II

The invention further deals with a calixpyrrole-based antitumor compound from Formula III:

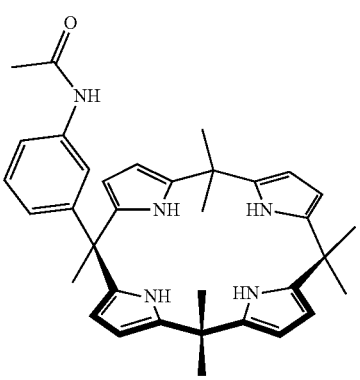

III also such antitumor compound being adapted to be used as such or derivatized to obtain its passive transport on tumor masses through an Enhanced Permeation and Retention, EPR, effect of the neoplastic vasculature.

The antitumor compound according to Formula III also has a derivative from Formula IV:

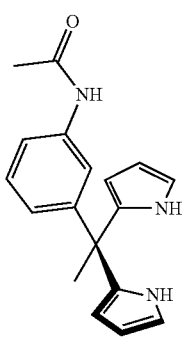

IV

The invention further deals with a calixpyrrole-based antitumor compound from Formula V:

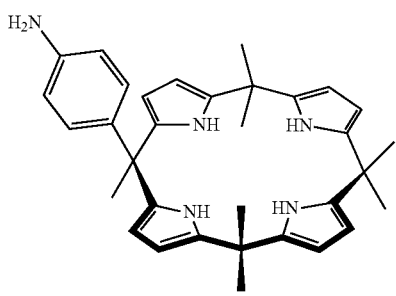

V also such antitumor compound being adapted to be derivatized to obtain its passive transport on tumor masses through an Enhanced Permeation and Retention, EPR, effect of the neoplastic vasculature.

The antitumor compound according to Formula V also has a derivative from Formula VI:

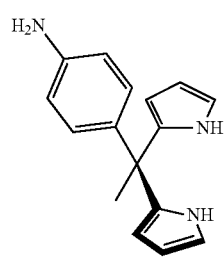

VI

The invention further deals with a calixpyrrole-based antitumor compound from Formula VII:

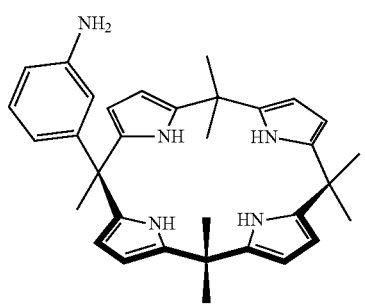

VII also such antitumor compound being adapted to be derivatized to obtain its passive transport on tumor masses through an Enhanced Permeation and Retention, EPR, effect of the neoplastic vasculature.

The antitumor compound according to Formula VII also has a derivative from Formula VIII:

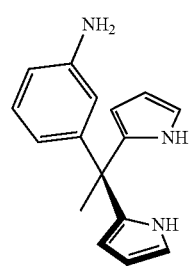

VIII

All above described antitumor compounds are adapted to be conjugated with peptides/antibodies for their active transport on tumor cells.

Moreover, such antitumor compounds are adapted to be inserted from formulations suitable to perform a selective delivery to tumor cells, such as for example covalent or non-covalent associations with nanomaterials or nanoparticles, preferably, but absolutely not in a limiting way, dendrimers, mesoporous silica, carbon nanotubes, organic polymers.

The invention further deals with an antitumor compound derivatized from the compound of Formula I, having a structure shown in Formula IX

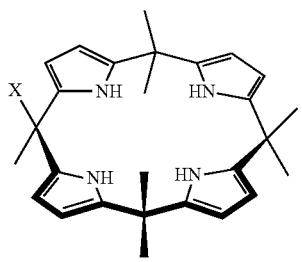

IX wherein the groups designated by X are: ArNHCOR' with R'=CH$_3$, O$_2$H$_5$, C$_3$H$_7$, phenyl or another aryl alkyl or heterocyclic group, Ar being a phenylene unit para-, meta- or ortho-substituted, to modulate the efficacy and/or the selectivity of the antitumor activity, namely used as means for connective the calixpyrrole derivative to a vector which allows an active or passive drug delivery.

Moreover, The invention further deals with an antitumor compound derivatized from the compound of Formula III, having a structure shown in Formula X

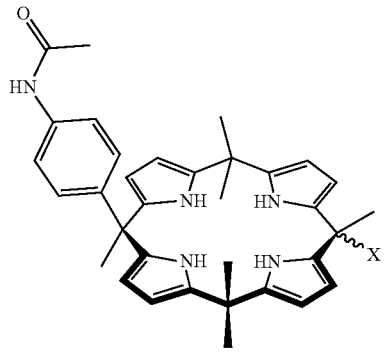

X wherein the groups designated by X are: ArNHCOR' with R'=CH$_3$, C$_2$H$_5$, C$_3$H$_7$, phenyl or another aryl alkyl or heterocyclic group, Ar being a phenylene unit para-, meta- or ortho-substituted, to modulate the efficacy and/or the selectivity of the antitumor activity, namely used as means for connective the calixpyrrole derivative to a vector which allows an active or passive drug delivery.

Still in particular, the invention further deals with an antitumor compound derivatized from the compound of Formula V, having a structure shown in Formula XI

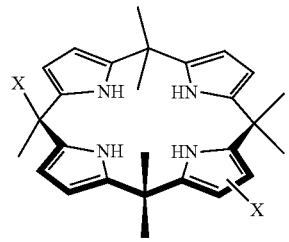

XI wherein the groups designated by X are: ArNHCOR' with R'=CH$_3$, C$_2$H$_5$, C$_3$H$_7$, phenyl or another aryl alkyl or heterocyclic group, Ar being a phenylene unit para-, meta- or ortho-substituted, to modulate the efficacy and/or the selectivity of the antitumor activity, namely used as means for connective the calixpyrrole derivative to a vector which allows an active or passive drug delivery.

Finally, the invention further deals with an antitumor compound derivatized from the compound of Formula VII, having a structure shown in XII

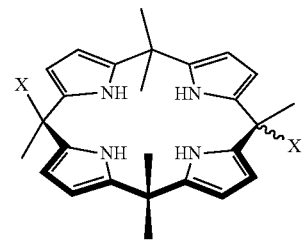

XII wherein the groups designated by X are: ArNHCOR' with R'=CH$_3$, C$_2$H$_5$, C$_3$H$_7$, phenyl or another aryl alkyl or heterocyclic group, Ar being a phenylene unit para-, meta- or ortho-substituted, to modulate the efficacy and/or the selectivity of the antitumor activity, namely used as means for connective the calixpyrrole derivative to a vector which allows an active or passive drug delivery.

The above described antitumor compounds, in particular those of Formulas I, III, V, VII, IX, X, XI and XII, being able, by passing the hematic-encephalic barrier, to be used in the treatment of brain metastasis from ovary tumors, lung tumors, estrogen-depending tumors, and tumors of neuro-endocrine origin, in addition to brain tumors.

EXAMPLES

The invention will further be described with reference to the following Examples and Tests, to be considered absolutely not limiting.

Herein below the first results are included for the tests obtained in vitro for the compounds of the invention, and for the preliminary tests obtained in vivo. The tested molecules have shown different activities on different cellular lines of tumor origin, and have been demonstrated as non-toxic in the preliminary tests in vivo.

Bio-information and chemo-information analyses have shown how the compounds of Formulas I and III are capable of easily passing the lipid membranes and of binding themselves to DNA forming adducts. Moreover, computational studies of the ADMET property, confirmed by preliminary pharmacy-kinetics studies, have pointed out how one of the molecules (compound from Formula I) is able to pass the hematic-encephalic barrier.

Cellular vitality tests have been performed by using the derivatives of Formulas VII, I and III on due ovary carcinoma lines (SKOV-3 and A2774), two mammary carcinoma lines (MCF-7 and MDAMB-231) and two pulmonary carcinoma lines (H727 and A549). The compounds of Formulas I and III have further been tested in liposomal nanoparticles (NP) in comparison with the pulmonary carcinoma lines H727. The pulmonary carcinoma lines have been used also as target for determining the genotoxicity of the compounds of Formulas I and III, for determining the type of cellular death, through flow cytometry analyses, and for a preliminary analysis in vivo with toxicity determination and pharmacy-kinetics estimation (compound from Formula I).

Moreover, a series of MTT tests have been performed on cellular lines A549 and SKOV-3 using the derivatives of Formulas VI, VIII, II and IV (such compounds can be considered as possible fragments of the macrocycles of Formulas V, VII, I and III) in order to demonstrate the absence of toxicity in case the molecule degrades.

Herein below the results obtained so far are included, wherein the Figure keys have the following references:

'107' corresponds to the compound of Formula I;
'118' corresponds to the compound of Formula II;
'563' corresponds to the compound of Formula III;
'813' corresponds to the compound of Formula IV;
'274' corresponds to the compound of Formula V;
'732' corresponds to the compound of Formula VI;
'391' corresponds to the compound of Formula VII; and
'691' corresponds to the compound of Formula VIII.

Obtained Results

Figure 1:
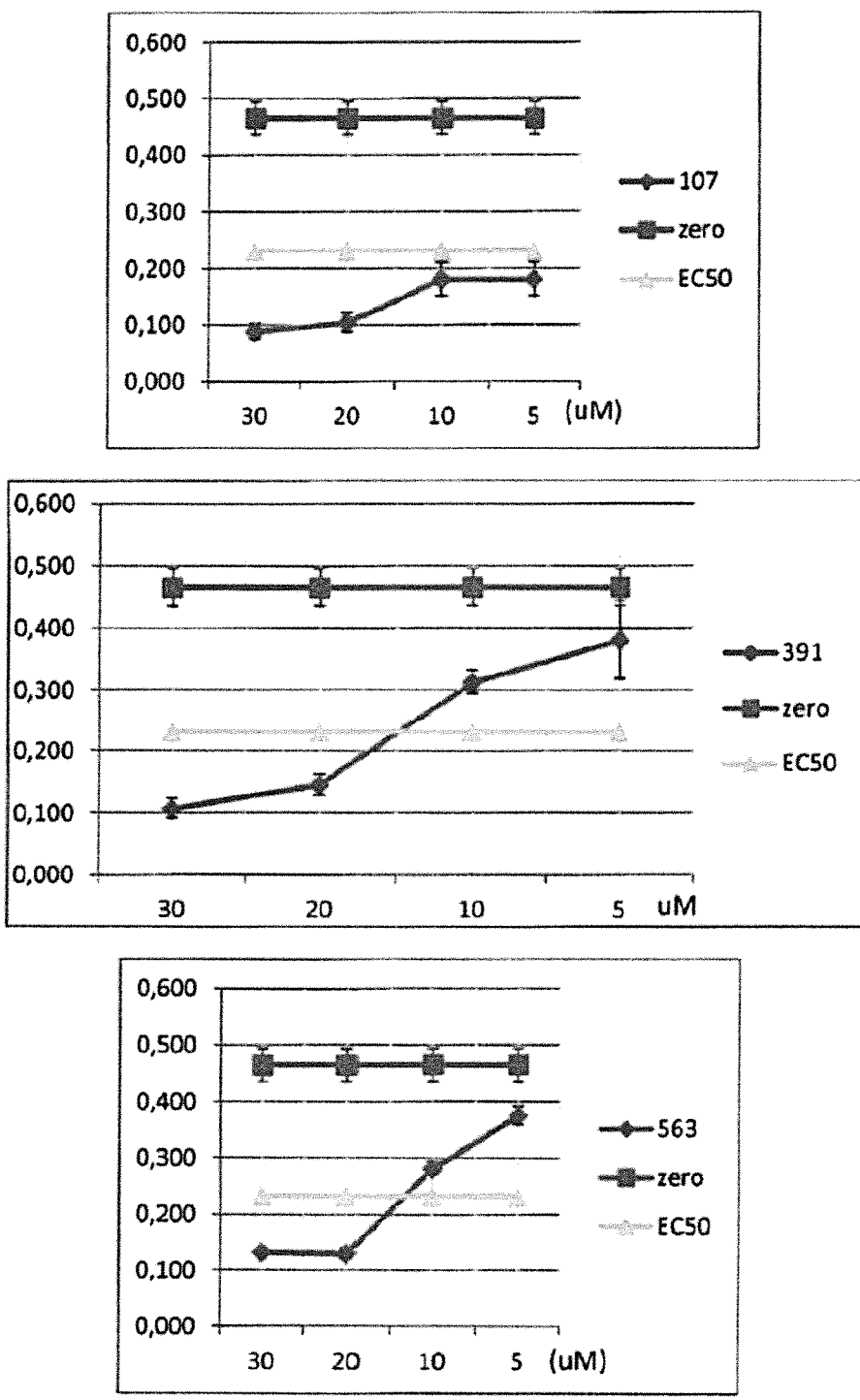
FIG. 1 shows the results of MTT tests performed on cellular lines deriving from ovary carcinoma SKOV-3 with the compounds of Formulas I, VII and III.
Figure 2:
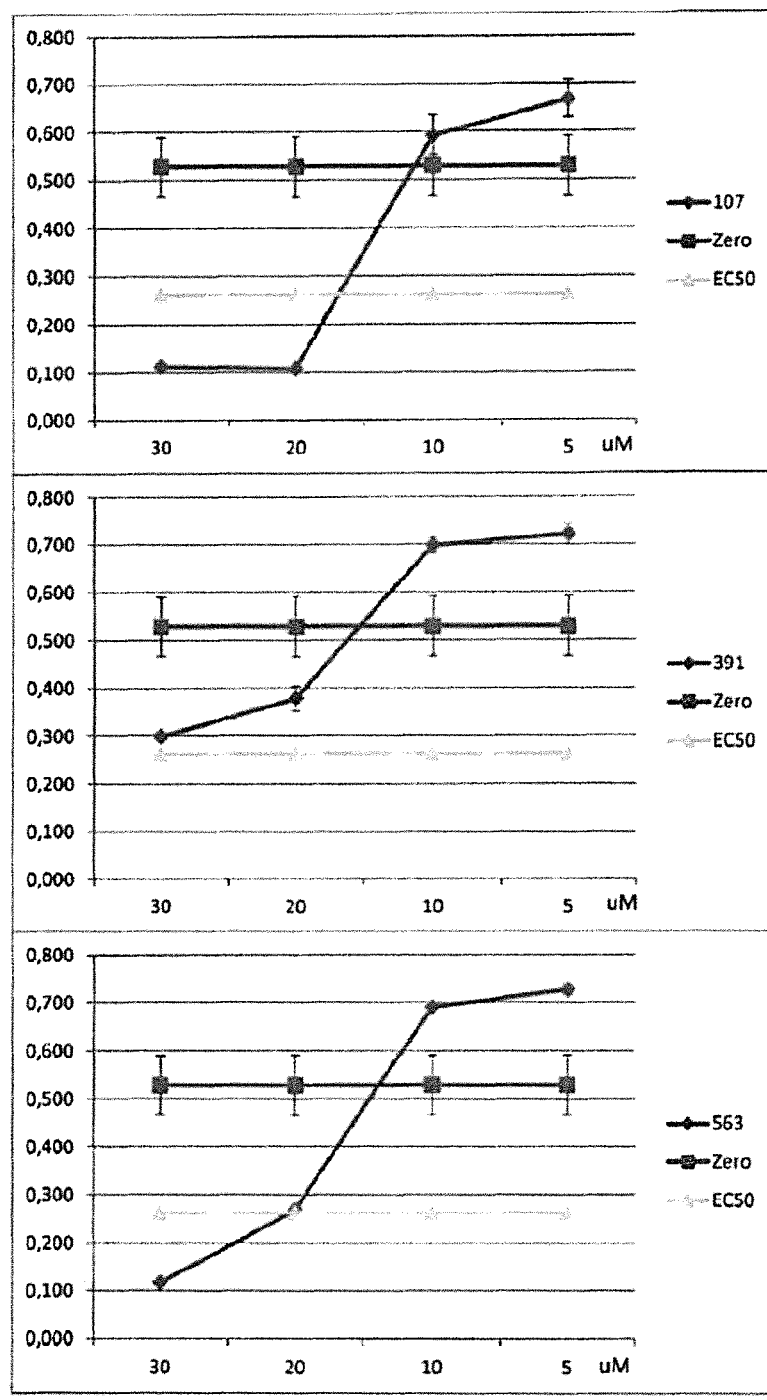
FIG. 2 shows the results of MTT tests performed on cellular lines deriving from ovary carcinoma 2774 with the compounds of Formulas I, VII and III.

The macrocycles of Formulas VII, I and III have been used in MTT tests on cellular lines derive from ovary carcinoma. In particular, as shown in FIG. 1, a high efficacy of the derivative from Formula I has been observed regarding the cellular lines deriving from ovary carcinoma SKOV-3 ($EC_{50}$ between 5 and 1 µM), while the derivatives of Formulas III and VII show a slightly smaller activity ($EC_{50}$ about 15 µM). Tests performed using the cellular line deriving from ovary carcinoma A2774, instead, have shown a lower activity for the derivative of Formulas I and III ($EC_{50}$ about 15 µM), while the derivative of Formula VII has not shown any activity, as pointed out in the graphs in FIG. 2. The selectivity shown by the derivative of Formula I compared with a specific cellular line surely needs to be further analyzed as regards its operating mechanism.

Figure 3:
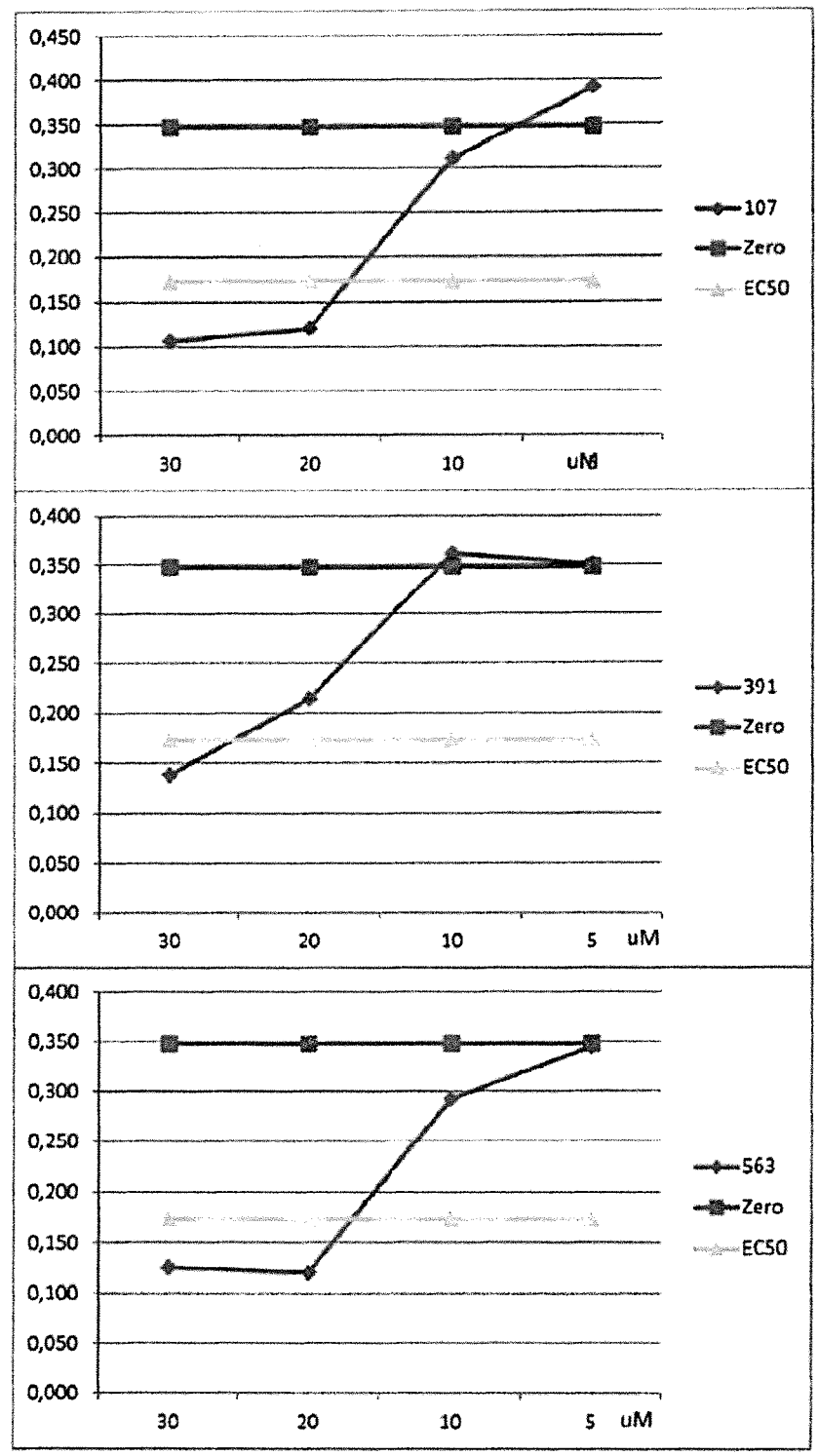
FIG. 3 shows the results of MTT tests performed on cellular lines deriving from mammary carcinoma MCF-7 with the compounds of Formulas I, VII and III.
Figure 4:
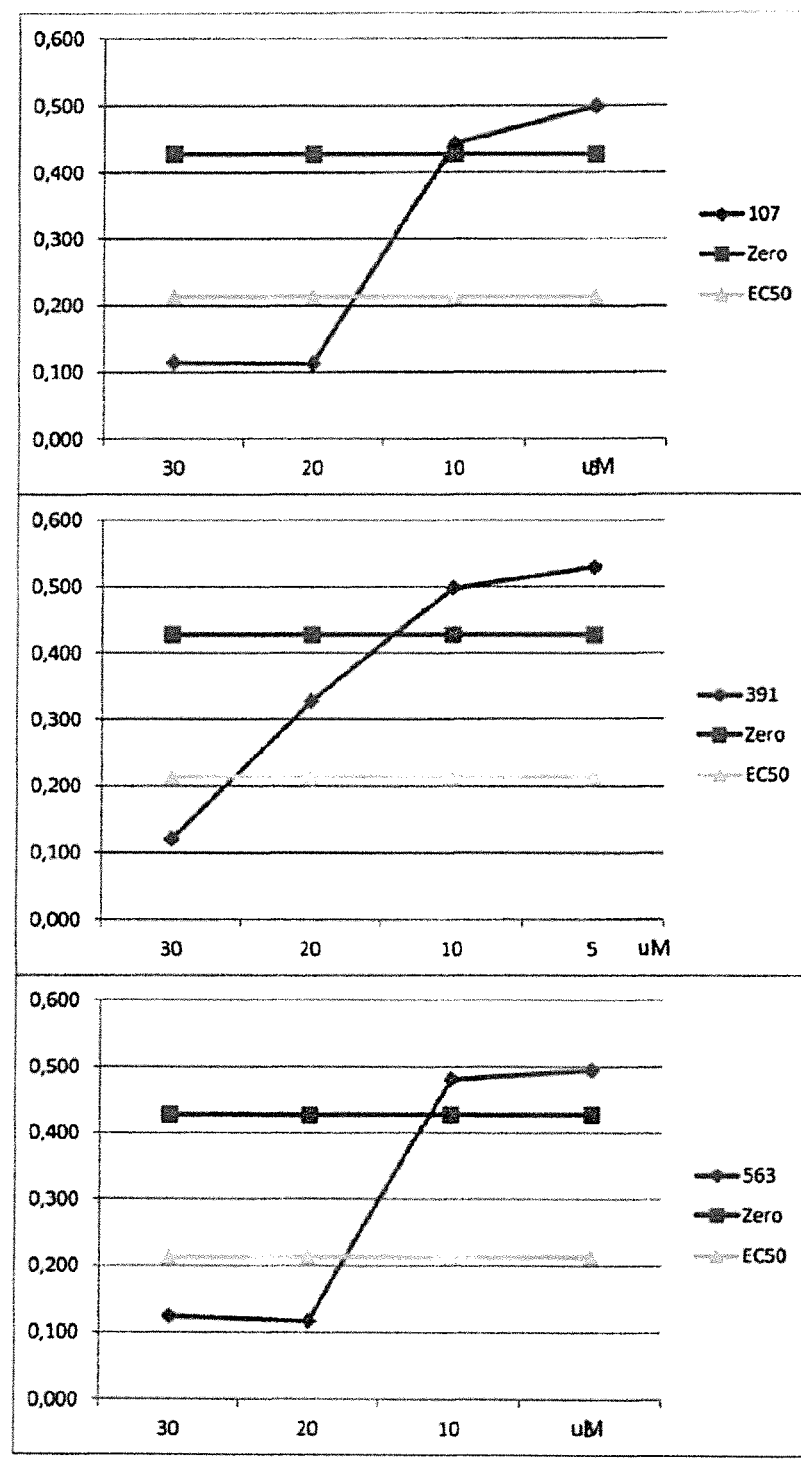
FIG. 4 shows the results of MTT tests performed on cellular lines deriving from mammary carcinoma MDAMB-231 with the compounds of Formulas I, VII and III.

MTT tests performed on mammary carcinoma lines MCF-7 and MDAMB-231 show that the derivatives of Formulas I, VII and III have a lower cytotoxicity than the one discovered in case of an ovary tumor. In particular, for both tumor cellular lines, the derivatives of Formulas I and III have $EC_{50}$ of about 20 µM, while the derivative of Formula VII has a $EC_{50}$ included between 20 and 30 µM, as shown in the graphs in FIG. 3 and FIG. 4.

Figure 5:
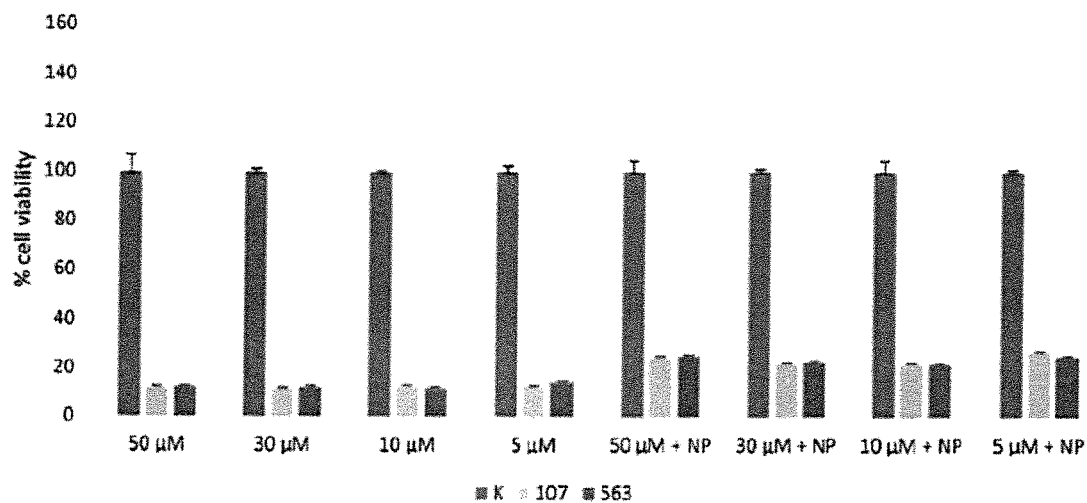
FIG. 5 shows the results of MTT tests performed on cellular lines deriving from pulmonary carcinoma H727 with the compounds of Formulas I and III, with K as control.
Figure 6:
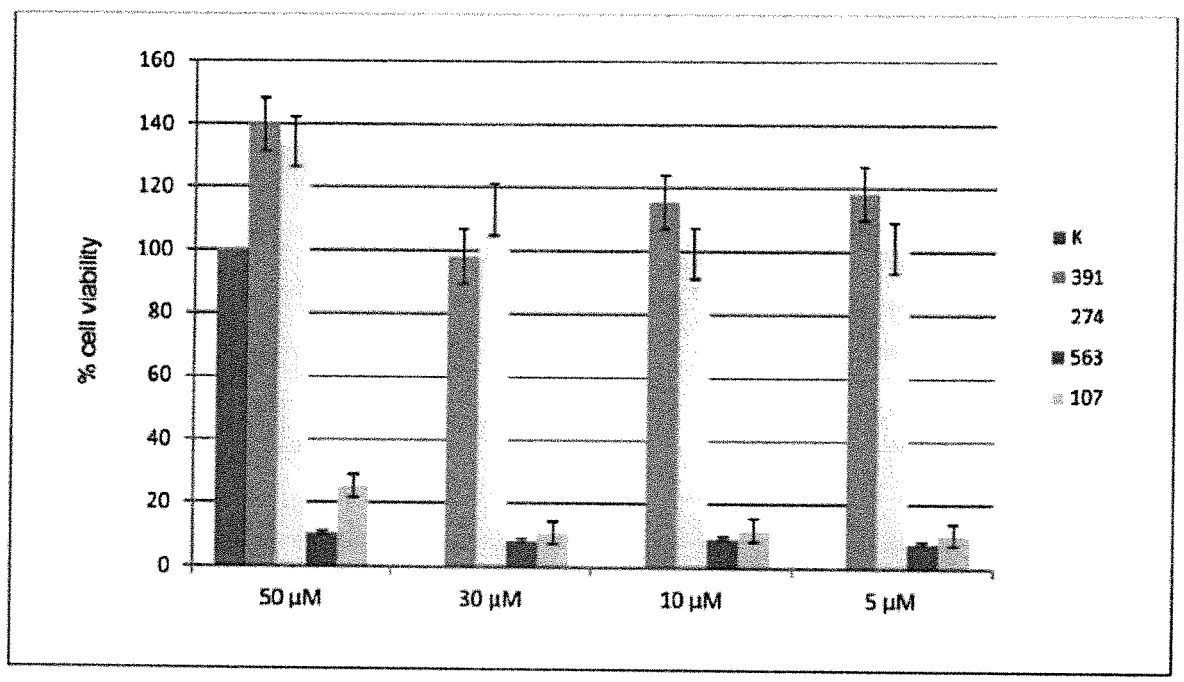
FIG. 6 shows the results of MTT tests performed on cellular lines deriving from pulmonary carcinoma A549 with the compounds of Formulas VII, V, III and I, with K as control.
Figure 7:
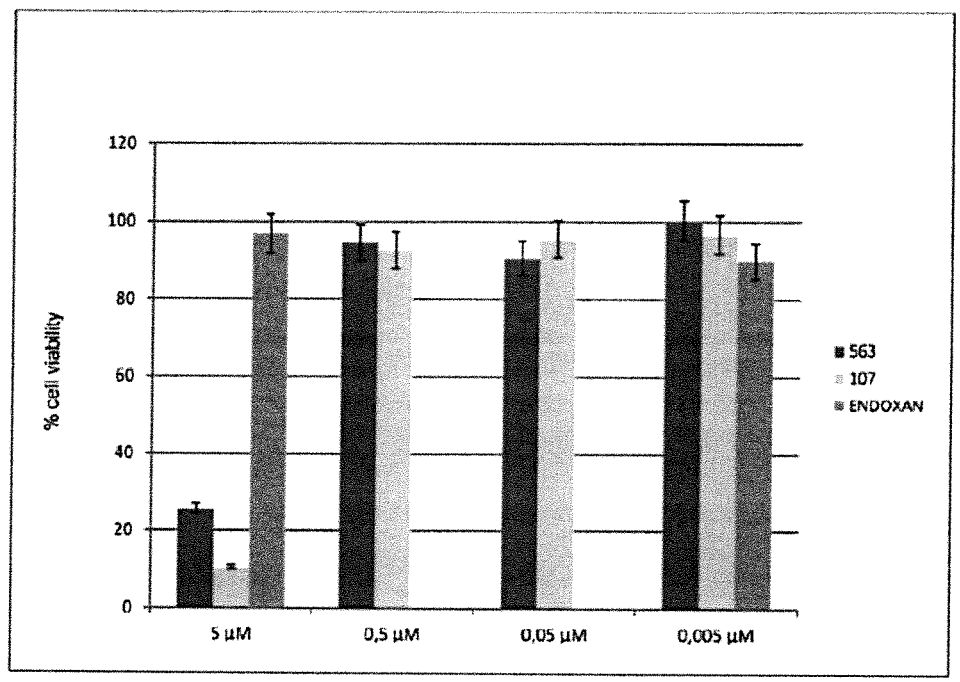
FIG. 7 shows the results of MTT tests performed on cellular lines deriving from pulmonary carcinoma A549, compared at various concentration of the compounds of Formulas I and III with the chemotherapeutic drug Endoxan (cyclophosphamide)

The derivatives of Formulas I and III have been used for a series of MTT tests at different concentrations, as such or from a formulation of lipid nanoparticles (NP), using cellular lines deriving from pulmonary carcinoma H727. The obtained results show that such derivatives show their maximum efficacy already at the lowest doses being used (5 µM), while the use of lipid nanoparticles (NP) decreases the efficacy of the compounds, increasing the cellular vitality (FIG. 5). Similar results are obtained with the derivatives of Formulas I and III using as target the cellular lines deriving from pulmonary carcinoma A549; it must be further pointed out that, compared with these cellular lines, the derivatives of Formulas V and VII seem not show any efficacy (FIG. 6). Moreover, the derivatives of Formulas I and III appear even more efficient than the known chemotherapeutic drug Endoxan (cyclophosphamide) (FIG. 7).

Figure 8:
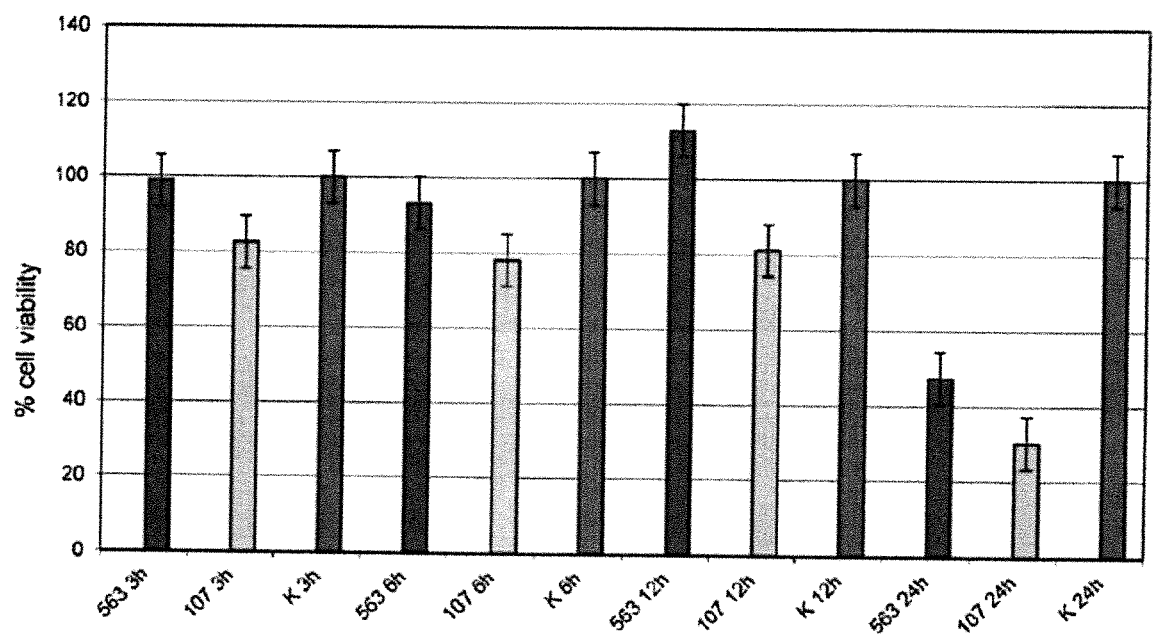
FIG. 8 shows the results of the control of the cell vitality at 3, 6, 12 and 24 hours after administration of the derivatives of Formulas I and III, with K as control.

The necessary period to have the highest rate of cellular mortality is 24 hours from the administration, while in the first 12 hours the cellular mortality is kept practically constant (FIG. 8).

Figure 9:
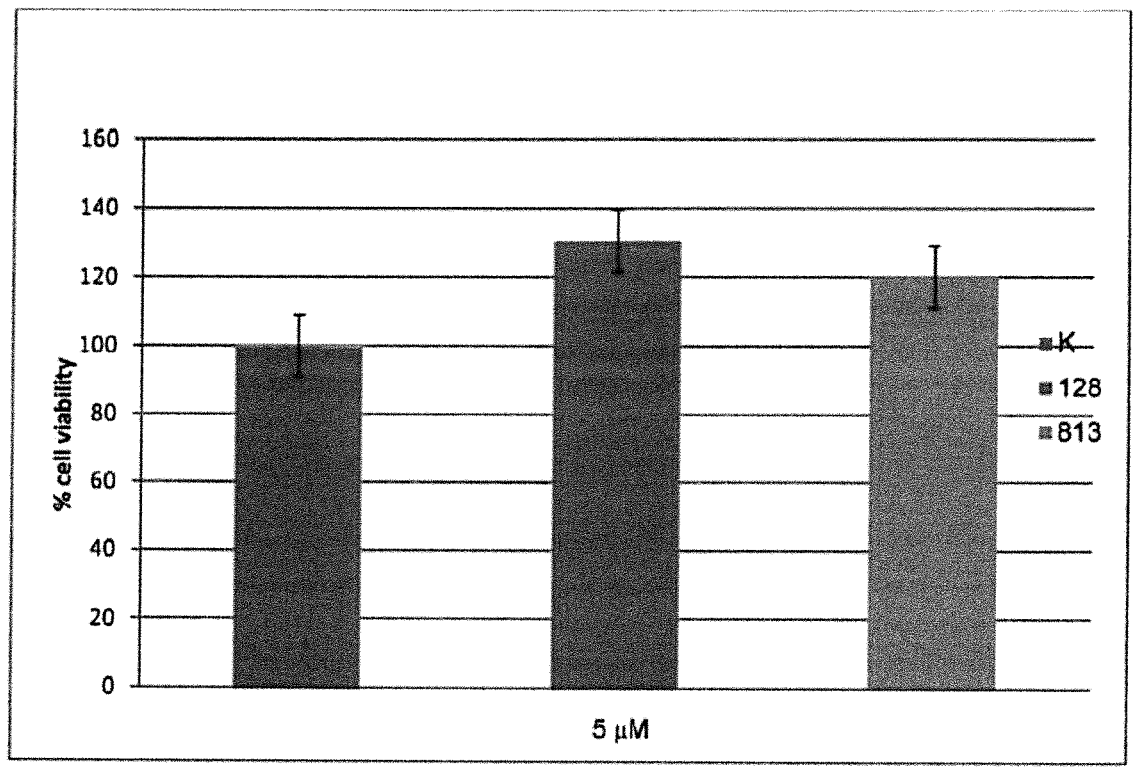
FIG. 9 shows the results of MTT tests performed on cellular lines deriving from pulmonary carcinoma A549 with the compounds of Formulas II and IV, with K as control.
Figure 10:
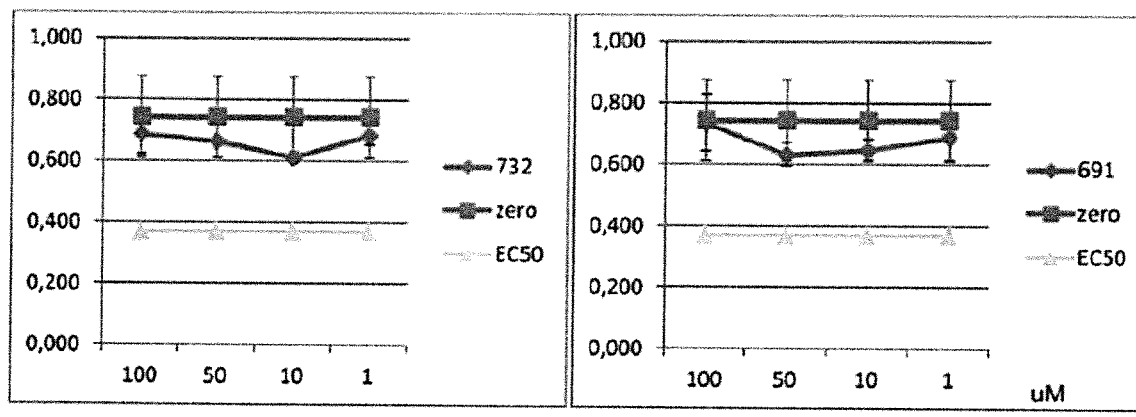
FIG. 10 shows the results of MTT tests performed on cellular lines deriving from ovary carcinoma SKOV-3 with the compounds of Formulas VI and VIII.

A series of MTT tests have been performed by using the derivatives of Formulas VI, VIII, II and IV (such compounds can be considered as possible fragments of the macrocycles of Formulas V, VII, I and III). In particular, the compounds of Formulas II and IV have not shown any activity on the cellular lines of pulmonary carcinoma A549 (FIG. 9), while the fragments of Formulas VI and VIII have been demonstrated as inefficient compared with the cellular lines of ovary carcinoma SKOV-3 (FIG. 10). The results of these MTT tests show how the cytotoxic activity of the compounds of the invention has to be ascribed to the complete structure of the macrocycle having the acetyl function and not to any isolated component thereof. This shows that the structure present in the derivatives of Formulas I and III has to be considered a "lead compound".

The analysis through flow cytometry performed on the cellular lines of pulmonary carcinoma A549 has shown how the apoptosis is the main death mechanism caused by the compounds of Formulas I and III. The cellular lines A549 treated with the compound of Formula I show 38.80% of apoptosis (9.05% early apoptosis and 29.75% late apoptosis) compared with a 9.30% of necrosis. The same cells treated with the compound of Formula III show 23.45% of total apoptosis (10.25% early apoptosis and 13.20% late apoptosis) against 4.75% of necrosis.

A series of COMET tests have been performed on the derivatives of Formulas V, VII, I and III, determining the percentage of fragmentation of DNA by the used receptor, with respect to standard K. In particular, in case of receptors of Formulas V and VII, at concentrations from 5 to 50 µM, a fragmentation is observed, while, under the same conditions, the compounds of Formulas I and III have not given any fragmentation of DNA (FIG. 11). These latter data are mainly affected by the fact that this technique is not able to detect dead cells, and, in case of compounds of Formulas I and III, such percentage, as previously seen, is relevant.

For the receptors of Formulas I and III, the adducts with DNA have been identified through 32P marking, using cellular lines of pulmonary carcinoma A549 (FIG. 12). The enrichment procedure has been performed through extraction with butanol: this shows that the receptor-DNA adducts being formed are characterized by a high molecular weight and the presence of aromatic rings and high lipophilicity. The presence of a higher number of adducts (see panels 3 and 74 of FIG. 12) shows a higher genotoxicity of the compound of Formula III with respect to the derivative of Formula I.

A preliminary analysis for the toxicity in vivo has been performed by using the compound of Formula I on NJ mice. Due to the particularly hydrophobic nature of such derivative, after various attempts to determine the best solvent mixture, which is non-toxic for the animal, but which contains an adequate concentration of receptor, it has been decided to administer the compound using a mixture containing 10% of DMSO in olive oil. Computational simulations showed a lethal oral dose ($LD_{50}$) equal to 383.26 mg/Kg. in order to experimentally determine a $LD_{50}$, a first dose of 5 mg/Kg has been injected subcutaneously, then it has been increased by 5 and finally by 50 times, without discovering particular effects on the mouse. Also the modification of the administration route from subcutaneous to intraperitoneal has not show any apparent effect on the animal. After 5 days, the mouse has been sacrificed and, through a HPLC/Mass analysis, the distribution of the compound inside the different compartments has been determined. The different tissues/organs (back sub-skin, spleen, omentum, heart, liver, brain, lung and kidney) have been removed, homogenized and analyzed. A high concentration of the compound of Formula I (determined through the computation of the peak area at m/z 546.31), corresponding to the analyzed compound [M-H]⁻), has been observed in the injection site (Area 532.875) and in the spleen (Area 196.233), but the biggest amount has been discovered in the omentum (Area 1.237.999). Lower concentrations have been discovered in the kidney (Area 120.117), in the lung (Area 32.514) and in the heart (Area 29.443). A minimum amount of the compound has been detected in the liver (Area 11.293). Finally, a small amount of the compound has been observed in the brain (Area 7.735): this means that the subject molecule, in spite of its sizes, is actually capable of passing the hematic-encephalic barrier.

In conclusion, from the preliminary data obtained so far, it can be stated that the calixpyrrole derivatives of Formulas I and III are potential "lead compounds" to be developed for the therapy of tumors, in particular for ovary tumors, lung tumors, estrogen-depending tumors, tumors of neuro-endocrine origin and brain tumors. The particular activity of the compound of Formula I on pulmonary tumor cells and its capacity of passing the hematic-encephalic barrier place the bases for a potential use of this compound for attacking brain metastases deriving from primary pulmonary tumors.

The invention claimed is:

1. An antitumor compound having a structure as shown in Formula IX:

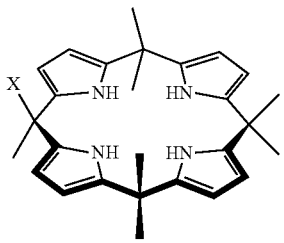

IX wherein X is: ArNHCOR' wherein R'=CH$_3$, C$_2$H$_5$, C$_3$H$_7$, phenyl or another aryl, alkyl or heterocyclic group, and wherein Ar being a phenylene unit para-, meta- or ortho-substituted with -NHCOR'.

2. The antitumor compound of claim 1, having a structure of Formula I:

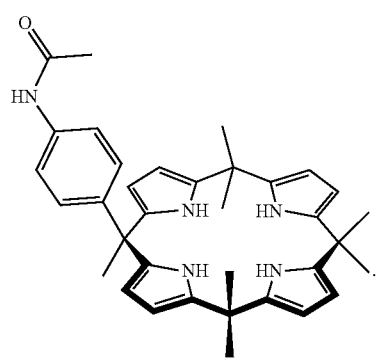

I

3. An antitumor compound of Formula II:

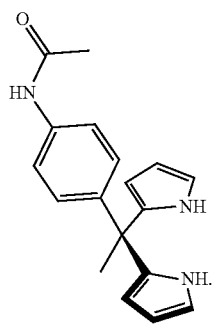

II

* * * * *